(12) United States Patent
Vouillamoz et al.

(10) Patent No.: US 11,287,776 B2
(45) Date of Patent: Mar. 29, 2022

(54) SYSTEMS AND METHODS FOR ABSORPTION/EXPANSION/CONTRACTION/MOVEMENT OF A LIQUID IN A TRANSPARENT CAVITY

(71) Applicant: Preciflex SA, Neuchâtel (CH)

(72) Inventors: Lucien Vouillamoz, Feusisberg (CH); Yves Ruffieux, St-Aubin (CH)

(*) Notice: Subject to any disclaimer, the term of this patent is extended or adjusted under 35 U.S.C. 154(b) by 461 days.

(21) Appl. No.: 15/301,441

(22) PCT Filed: Apr. 7, 2015

(86) PCT No.: PCT/IB2015/000448
§ 371 (c)(1),
(2) Date: Oct. 3, 2016

(87) PCT Pub. No.: WO2015/150910
PCT Pub. Date: Oct. 8, 2015

(65) Prior Publication Data
US 2017/0146956 A1    May 25, 2017

Related U.S. Application Data

(60) Provisional application No. 62/033,686, filed on Aug. 6, 2014, provisional application No. 61/985,492, filed
(Continued)

(51) Int. Cl.
| | |
|---|---|
| *G04B 45/00* | (2006.01) |
| *G04B 1/26* | (2006.01) |
| *G04C 17/00* | (2006.01) |
| *A61M 5/142* | (2006.01) |
| *G09F 13/24* | (2006.01) |
| *B65D 25/54* | (2006.01) |

(52) U.S. Cl.
CPC ......... *G04B 45/0069* (2013.01); *A61M 5/142* (2013.01); *B65D 25/54* (2013.01); *G04B 1/26* (2013.01); *G04C 17/00* (2013.01); *G09F 13/24* (2013.01)

(58) Field of Classification Search
CPC ..... G09F 13/24; G04B 37/02; G04B 45/0069; B65D 25/54; B65D 25/56
See application file for complete search history.

(56) References Cited

U.S. PATENT DOCUMENTS

| | | |
|---|---|---|
| 2,031,409 A | 2/1936 | Fioravanti |
| 3,388,490 A | 6/1968 | Stechemesser |
| (Continued) | | |

FOREIGN PATENT DOCUMENTS

FR    1552838 A    1/1969

OTHER PUBLICATIONS

International Search Report of International Patent Application No. PCT/IB2016/000448, published on Oct. 8, 2015.

*Primary Examiner* — Don M Anderson
*Assistant Examiner* — Jennifer Castriotta
(74) *Attorney, Agent, or Firm* — Da Vinci Partners LLC; John Moetteli

(57) ABSTRACT

A thermal compensation system is provided for a liquid-filled inflexible chamber of a device. The chamber has at least one exposed, at least partially transparent surface allowing an outside observer to observe at least one liquid and comprises a mechanism accommodating thermal expansion and/or contraction of the liquids. The mechanism is disposed so as to be substantially invisible to the observer.

8 Claims, 3 Drawing Sheets

Related U.S. Application Data on Apr. 29, 2014, provisional application No. 61/974,448, filed on Apr. 3, 2014.

(56) References Cited

U.S. PATENT DOCUMENTS

| | | | | |
|---|---|---|---|---|
| 3,779,093 A | * | 12/1973 | Hetzel | G04B 11/04 74/142 |
| 4,080,781 A | * | 3/1978 | Klingenberg | G04B 37/02 206/18 |
| 2007/0280839 A1 | | 12/2007 | Furetta | |
| 2012/0155230 A1 | | 6/2012 | Patt | |

* cited by examiner

SYSTEMS AND METHODS FOR ABSORPTION/EXPANSION/CONTRACTION/MOVEMENT OF A LIQUID IN A TRANSPARENT CAVITY

CROSS REFERENCE TO RELATED APPLICATIONS

This application is the National Stage of International Application No. PCT/IB2015/000448, filed Apr. 7, 2015, which claims benefit under 35 USC § 119(a), to U.S. provisional patent application Ser. No. 61/974,448, filed Apr. 3, 2014, US provisional patent application Ser. No. 62/033,686, filed Aug. 6, 2014, and U.S. provisional patent application Ser. No. 61/985,492, filed Apr. 29, 2014.

COPYRIGHT & LEGAL NOTICE

A portion of the disclosure of this patent document contains material which is subject to copyright protection. The Applicant has no objection to the facsimile reproduction by anyone of the patent document or the patent disclosure as it appears in the Patent and Trademark Office patent file or records, but otherwise reserves all copyright rights whatsoever. Further, no references to third party patents or articles made herein are to be construed as an admission that the present invention is not entitled to antedate such material by virtue of prior invention.

BACKGROUND OF THE INVENTION

This invention relates to systems and methods for timepieces that include absorption/expansion/movement of a liquid in a transparent cavity, particularly in wristwatches.

SUMMARY OF THE INVENTION

A thermal compensation system is provided for a liquid-filled inflexible chamber of a device. The chamber has at least one exposed, at least partially transparent surface allowing an outside observer to observe at least one liquid and comprises a mechanism accommodating thermal expansion and/or contraction of the liquid(s). The mechanism is disposed so as to be substantially invisible to the observer.

The system prevents the thermal expansion and/or contraction of the liquid(s) from compromising (i.e., breaking) the closed inflexible chamber in which they are contained.

At least one of such liquid is colored or has a suspension of particulate therein or has the same refractive index as the substrate (glass or polymer)

In one variant, the invention provides a thermal expansion system that includes a chamber, and a liquid, the chamber includes a visible system and a non-visible system, the non-visible system is disposed underneath the visible system. The non-visible system is filled with a gas, and the visible system is filled with the liquid.

In yet a further variant of the invention, a thermal expansion system is provided that includes an inner chamber. The inner chamber is filled with a liquid, and the inner chamber further includes at least one inner chamber wall in which a soft, compressive/expansive material is disposed in a non-visible portion of the system.

In another embodiment, at least one inner chamber wall has, on at least a portion of a surface thereof, a soft, compressive/expansive material disposed thereon.

In yet a further aspect of the invention, a thermal expansion system is provided that includes a chamber. The chamber is formed from at least two glass or polymer wafers, and the chamber includes at least two cavities. The at least two cavities are separated by one or more transparent members forming two separate cavities. In one variant, a transparent membrane is disposed between and attached to the two glass or polymer wafers to form fluid tight/gas tight cavities. One of the cavities is filled with a liquid, while the second cavity provides an access hole for access to ambient pressure.

It is appreciated that these and other aspects of the invention are further described in the detailed description, drawings and claims of the instant application.

Those skilled in the art will appreciate that elements in the Figures are illustrated for simplicity and clarity and have not necessarily been drawn to scale. For example, dimensions may be exaggerated relative to other elements to help improve understanding of the invention and its embodiments. Furthermore, when the terms 'first', 'second', and the like are used herein, their use is intended for distinguishing between similar elements and not necessarily for describing a sequential or chronological order. Moreover, relative terms like 'front', 'back', 'top' and 'bottom', and the like in the Description and/or in the claims are not necessarily used for describing exclusive relative position. Those skilled in the art will therefore understand that such terms may be interchangeable with other terms, and that the embodiments described herein are capable of operating in other orientations than those explicitly illustrated or otherwise described.

DETAILED DESCRIPTION OF THE PREFERRED EMBODIMENT

The following description is not intended to limit the scope of the invention in any way as it is exemplary in nature, serving to describe the best mode of the invention known to the inventors as of the filing date hereof. Consequently, changes may be made in the arrangement and/or function of any of the elements described in the exemplary embodiments disclosed herein without departing from the spirit and scope of the invention.

Figure 1:
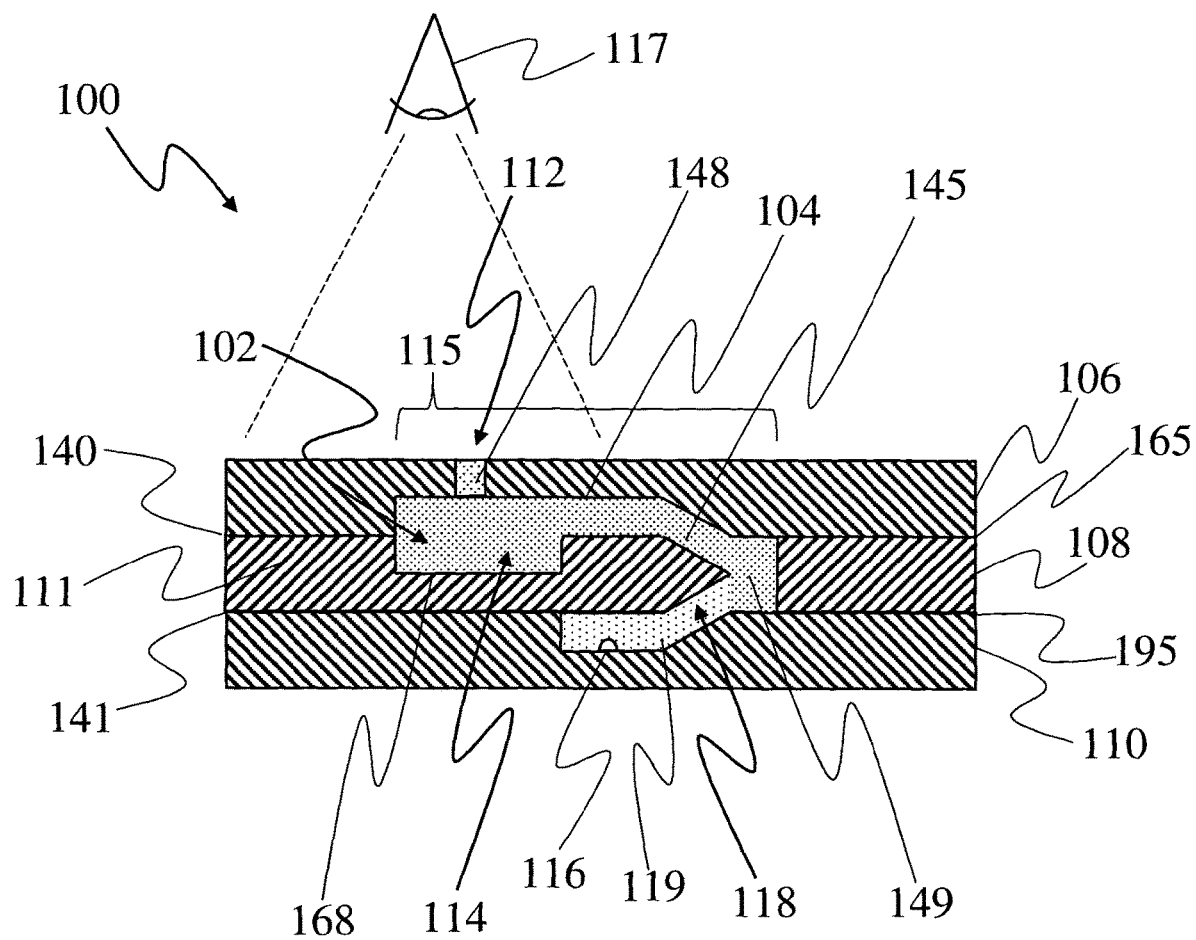
FIG. 1 is a schematic of a system compensating for the thermal expansion and/or contraction of a liquid of the invention.

Referring to FIG. 1, a system 100 compensates for thermal expansion and/or contraction of an encapsulated liquid 102 contained in a fluidic chamber 104 typically formed by the bonding of two or more glass or polymer wafers 106, 108, 110 together. A suitable bonding process is fusion bonding, although other methods may be used. The glass or polymer wafers 106, 108, 110 are transparent, translucent, or colored, or a combination thereof, as desired. It is appreciated that the system 100 provides a desired aesthetic appearance suitable for wristwatches or other luxury jewelry apparel. The liquid 102 is preferably a colored or particulated liquid or has the same refractive index as the substrate (glass or polymer) liquid in a variant of the invention, and displacement of the liquid 102 is dependent on the liquid's thickness or viscosity. Liquid 102 is homogeneous of one variant of the invention, however, liquid 102 may be heterogeneous in another variant of the invention (e.g., having a suspension of a particulate such as gold leaf), for aesthetic effect. The fluidic chamber 104 is formed by the bonding of, for example, three glass or polymer wafers, 106, 108, 110 at bonding junctures 165, 195. Where the wafer is not integral with wafer 108 and appropriately machined or processed, a fourth wafer 111 is also provided, and bonded to wafers 106, 110 at bonded junctures 140, 141. Glass or polymer wafer 111 has a specific geometry and three dimensional profile that optionally includes recess 168 forming a larger cavity 114. Larger cavity 114 then is in fluid communication with passage way 145 which optionally has a bend 149 which joins passage way 119 forming a suitable "U" shaped cavity within the system 100. The liquid 102 is injected into the fluidic chamber 104 through access hole 112 which is closed with plug 148, optionally a glass or polymer plug, after filling. At the end of the process, the fluidic chamber 104 obtained is composed of a main visible system 115 filled with the liquid 102, and a gas filled chamber extension 116. Chamber extension 116 is disposed below the main fluidic chamber 104 in relation to a field of view of an observer/user 117, and the chamber extension 116 is filled with a gas 118. It is appreciated that the invention provides for both a visible and invisible portions of the mechanism simultaneously to a user's field of view in one variant. During a liquid thermal expansion, the gas 118 is compressed by the fluid 102 leading to additional space for the liquid 102 under the main fluidic chamber 104. The opposite occurs as the liquid contracts upon cooling. It may be added that the system must be dimensioned such that the gas 119 does not reach the limit of the extension chamber 116 to the minimum operational temperature of the system (e.g. −20° C.), preventing the gas going out of the chamber 116.

Figure 2:
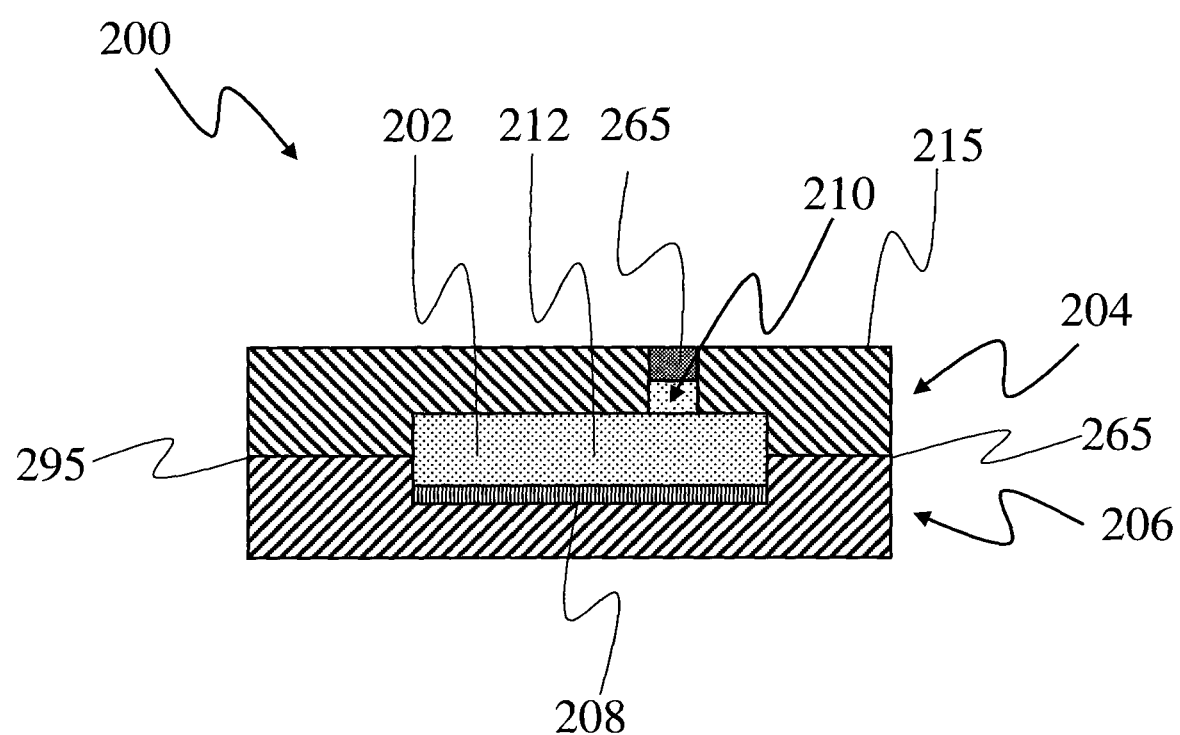
FIG. 2 is a schematic of a variant of a system for compensating for the thermal expansion and/or contraction of a liquid of the invention.

Referring to FIG. 2, a variant of the invention includes a cut away view of system 200. Fluidic chamber 202 is formed by the bonding of two or more glass or polymer wafers, 204, 206. The bonding creates at least two bonded junctures 265, 295. A soft, compressible/expandable material 208 is inserted or injected through the chamber access hole 210 placed on at least one side 215 of the wafer 204, the hole 210 traversing the entire width of the wafer 204. The fluidic chamber 202 is entirely filled with the preferably colored or particulated liquid 212 or is a liquid having the same refractive index as the substrate (glass or polymer) through the access hole 210 which is closed and sealed with a plug 265, preferably made of glass or polymer, after filling. Optionally, a second access hole (not shown) to fluidic chamber 202 is also provided to facilitate the evacuation of the gas remaining inside the cavity. The optional second access hole is also closed with a plug, e.g. a glass or polymer plug, after the filling process. Of course, it is appreciated that a plurality of access holes may be provided through wafers 204 and/206 and then closed and sealed as necessary, in another variant of the invention. In operation and during fluid thermal expansion, the pressure generated by the liquid 212 compresses the soft material 208 creating additional space for the liquid 212. The opposite occurs during thermal contraction of the liquid 212. The soft material 208 is preferably a closed cell sponge, but other materials exist that do not contain gas that are nonetheless compressible in water. In a sponge variant, the closed cell structure is necessary to avoid the sponge 208 absorbing the liquid and therefore becoming essentially incompressible. Further, in order to permit bonding by fusion bonding, the compressibility of the soft material must be greater than its resistance to fusion bonding.

Figure 3:
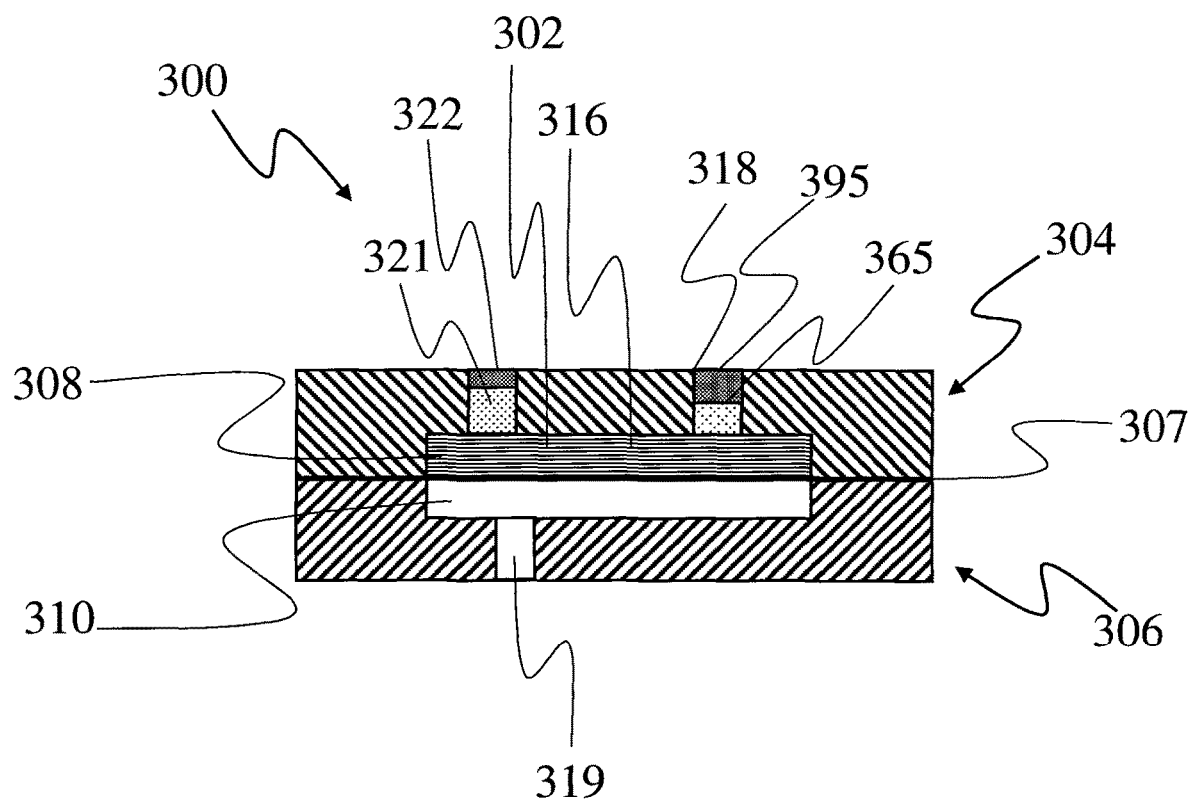
FIG. 3 is a schematic of another variant of a system for compensating for the thermal expansion and/or contraction of a liquid of the invention.

Another variant of the invention, system 300, is illustrated FIG. 3, The fluidic chamber 302 is formed by bonding, preferably fusion bonding, of two or more glass or polymer wafers 304, 306, and one transparent membrane 307 placed between the two or more glass or polymer wafers 304, 306. In this configuration, the fluidic chamber 302 is separated in two or more sections 308, 310 that are airtight/liquid-tight in one variant. The two sections 308, 310 are accessible by holes 395, 319 in the wafer 304, and wafer 306. Section 308 is entirely filled with a preferably colored or particulated liquid 316 or a liquid which has the same refractive index as the substrate (glass or polymer), while section 310 is filled with air or other suitable gas. After the filling process, the access hole 395 used to inject the liquid 316 is closed and sealed with a plug 365, e.g. a glass or polymer plug, with the other access hole 319 remaining opened. As described above in FIG. 2, on the side 318 of the wafer 304 for liquid injection, a second optional access hole 321 is provided to facilitate the evacuation of the gas remaining inside the cavity of section 308. The optional second access hole 321 is also closed and sealed with a glass plug 322 after the filling process. In operation and during fluid thermal expansion of the liquid 316, the pressure generated by the liquid 316 deforms the membrane 307 creating additional space for the fluid 316. Both open and closed systems are provided in different variants of the invention described herein.

In the accompanying description, it is appreciated that the system 100, 200, 300 for a device includes a mechanism and/or subsystem to provide for a thermal expansion and contraction of a preferably colored or particulated liquid, or a liquid which has the same refractive index as the substrate (glass or polymer) in a chamber as described herein in a manner that is non-visible to a user.

The invention and variants thereof are further described in the accompanying claims and drawings.

In an advantage of the invention, the system 100, 200, 300 provide a way to display a vivid fluid filled cavity without concern that thermal expansion or contraction of the fluid will cause damage to the chamber in which it is contained, thus avoiding leaks and cracks.

In a further advantage, the system 100, 200, 300 may be filled with a liquid having a particulate suspended therein, such as gold leaf, which provides a highly attractive decorative effect.

In a further advantage, the system 100, 200, 300 provides an efficient means of fabrication through the bonding together of flat wafers.

In a still further advantage, the system 100, 200, 300 requires little space or volume and so may be integrated into small devices such as watches. Further, effects can be created that bring to mind the association with luxurious and innovative products.

The liquid 102 may be static and so purely decorative or moved in a system that might have a technical function, such as the indication of time. The system may even be a closed system, driven by a pump. Ferromagnetics may be used to move the liquid. A simple electric pump inside the closed system may also be used, where power is supplied through electrodes that traverse the closed system boundaries. The phenomena of electrowetting may also be used to move the fluid.

As used herein, the terms "comprises", "comprising", or variations thereof, are intended to refer to a non-exclusive listing of elements, such that any apparatus, process, method, article, or composition of the invention that comprises a list of elements, that does not include only those elements recited, but may also include other elements described in the instant specification. Unless otherwise explicitly stated, the use of the term "consisting" or "consisting of" or "consisting essentially of" is not intended to limit the scope of the invention to the enumerated elements named thereafter, unless otherwise indicated. Other combinations and/or modifications of the above-described elements, materials or structures used in the practice of the present invention may be varied or adapted by the skilled artisan to other designs without departing from the general principles of the invention. The patents and articles mentioned above are hereby incorporated by reference herein, unless otherwise noted, to the extent that the same are not inconsistent with this disclosure.

Other characteristics and modes of execution of the invention are described in the appended claims. Further, the invention should be considered as comprising all possible combinations of every feature described in the instant specification, appended claims, and/or drawing figures which may be considered new, inventive and industrially applicable.

Copyright may be owned by the Applicant(s) or their assignee and, with respect to express Licensees to third parties of the rights defined in one or more claims herein, no implied license is granted herein to use the invention as defined in the remaining claims. Further, vis-à-vis the public or third parties, no express or implied license is granted to prepare derivative works based on this patent specification, inclusive of the appendix hereto.

Additional features and functionality of the invention are described in the claims appended hereto. Such claims are hereby incorporated in their entirety by reference thereto in this specification and should be considered as part of the application as filed.

Multiple variations and modifications are possible in the embodiments of the invention described here. Although certain illustrative embodiments of the invention have been shown and described here, a wide range of changes, modifications, and substitutions is contemplated in the foregoing disclosure. While the above description contains many specific details, these should not be construed as limitations on the scope of the invention, but rather exemplify one or another preferred embodiment thereof. In some instances, some features of the present invention may be employed without a corresponding use of the other features. Accordingly, it is appropriate that the foregoing description be construed broadly and understood as being illustrative only, the spirit and scope of the invention being limited only by the claims which ultimately issue in this application.

What is claimed is:

1. A system for compensation for thermal expansion and/or contraction of a liquid contained within a chamber, the liquid and an expandable barrier being disposed between a first substantially flat barrier and a second barrier, wherein the expandable barrier is sealingly affixed to and extends from the first substantially flat barrier so as to define the chamber therebetween in which the liquid is permanently encapsulated and in which at least one closeable access hole is provided into its interior, and wherein the liquid is in substantial part visible through the first substantially flat barrier.

2. The system of claim 1, whereby, the system is a closed system.

3. The system of claim 1, in which the chamber further comprises a sealed gas filled chamber extension portion disposed on an opposite side of the expandable barrier from the substantially flat barrier.

4. The system of claim 3, in which the gas filled chamber extension portion is disposed behind a visible portion of the chamber with respect to a field of view of a user.

5. The system of claim 4, wherein a volume of the gas changes during a liquid thermal expansion, by virtue of the liquid requiring additional space within the sealed chamber.

6. A system according to claim 1 wherein, at least a portion of the sealed liquid-filled chamber has a visible light property, the visible light property selected from the group consisting of a transparent visible light property, a translucent visible light property and a colored visible light property.

7. The system of claim 1, wherein the first substantially flat surface is substantially transparent, allowing the liquid to be visible.

8. A system for compensation for thermal expansion and/or contraction of a liquid contained within a chamber, the liquid and an expandable barrier being disposed between a first substantially transparent barrier and a second barrier, wherein the expandable barrier is sealingly affixed to and extends from the first substantially transparent barrier so as to define the chamber therebetween in which the liquid is permanently encapsulated and in which at least one closeable access hole is provided into its interior, which hole is closed to seal the chamber, and wherein the liquid is in substantial part visible through the first substantially transparent barrier.

* * * * *